(12) United States Patent
Kim et al.

(10) Patent No.: US 11,995,820 B2
(45) Date of Patent: May 28, 2024

(54) METHOD AND APPARATUS FOR AUTOMATED DETECTION OF LANDMARKS FROM 3D MEDICAL IMAGE DATA BASED ON DEEP LEARNING

(71) Applicant: IMAGOWORKS INC., Seoul (KR)

(72) Inventors: Youngjun Kim, Seoul (KR); Hannah Kim, Seoul (KR)

(73) Assignee: IMAGOWORKS INC., Seoul (KR)

( * ) Notice: Subject to any disclaimer, the term of this patent is extended or adjusted under 35 U.S.C. 154(b) by 0 days.

(21) Appl. No.: 17/295,916

(22) PCT Filed: May 26, 2020

(86) PCT No.: PCT/KR2020/006789
§ 371 (c)(1),
(2) Date: May 21, 2021

(87) PCT Pub. No.: WO2021/210723
PCT Pub. Date: Oct. 21, 2021

(65) Prior Publication Data
US 2023/0024671 A1   Jan. 26, 2023

(30) Foreign Application Priority Data
Apr. 16, 2020   (KR) ........................ 10-2020-0045924

(51) Int. Cl.
*G06T 7/00*      (2017.01)
*G06T 15/08*     (2011.01)
(Continued)

(52) U.S. Cl.
CPC ............ *G06T 7/0012* (2013.01); *G06T 15/08* (2013.01); *G06T 15/20* (2013.01); *G06V 10/25* (2022.01);
(Continued)

(58) Field of Classification Search
CPC ......... G06T 7/00; G06T 7/0012; G06T 15/08; G06T 15/20; G06T 2207/30008;
(Continued)

(56) References Cited

U.S. PATENT DOCUMENTS 9,025,858 B2 *   5/2015   Seong .................... G06T 19/00
                                                       382/128
11,087,871 B2 *  8/2021   Kim ...................... A61C 19/04

FOREIGN PATENT DOCUMENTS

CN          101882326 A       11/2010
KR       10-2012-0086084 A     8/2012
(Continued)

OTHER PUBLICATIONS

International search report dated Jan. 15, 2021.
(Continued)

*Primary Examiner* — Tuan H Nguyen
(74) *Attorney, Agent, or Firm* — LEEPI

(57) ABSTRACT

A method for automated detection of landmarks from 3D medical image data using deep learning according to the present inventive concept, the method includes receiving a 3D volume medical image, generating a 2D intensity value projection image based on the 3D volume medical image, automatically detecting an initial anatomical landmark using a first convolutional neural network based on the 2D intensity value projection image, generating a 3D volume area of interest based on the initial anatomical landmark and automatically detecting a detailed anatomical landmark using a second convolutional neural network different from the first convolutional neural network based on the 3D volume area of interest.

21 Claims, 14 Drawing Sheets

(51) Int. Cl.
*G06T 15/20* (2011.01)
*G06V 10/25* (2022.01)
*G06V 10/82* (2022.01)

(52) U.S. Cl.
CPC .... *G06V 10/82* (2022.01); *G06T 2207/30008* (2013.01); *G06T 2207/30036* (2013.01); *G06V 2201/07* (2022.01)

(58) Field of Classification Search
CPC .......... G06T 2207/30036; G06V 10/25; G06V 10/82; G06V 2201/07
See application file for complete search history.

(56) References Cited

FOREIGN PATENT DOCUMENTS

| KR | 10-1952887 B1 | 6/2019 | | |
|---|---|---|---|---|
| KR | 10-2015223 | * | 10/2019 | ............. G16H 50/20 |
| KR | 10-2015223 B1 | | 10/2019 | |
| KR | 10-2020-0023703 A | | 3/2020 | |

OTHER PUBLICATIONS

Extended European search report dated May 10, 2023.
A Cascade Regression Model for Anatomical Landmark Detection, Zimeng Tan, et al., STACOM 2019, LNCS 12009, pp. 43-51, 2020.
Btrfly Net: Vertebrae Labelling with Energy Based Adversarial Learning of Local Spine Prior, Anjany Sekuboyina, et al., MICCAI 2018, LNCS 11073, pp. 649-657, 2018.
Automatic Three-Dimensional Cephalometric Annotation System Using Three-Dimensional Constitutional Neural Networks, Sung Ho Kang, et al.
Automatic Cephalometric Landmark Detection on X-ray Images Using a Deep-Learning Method, Yu Song, et al., Appl, Sci. 2020, 10, 2547.

* cited by examiner

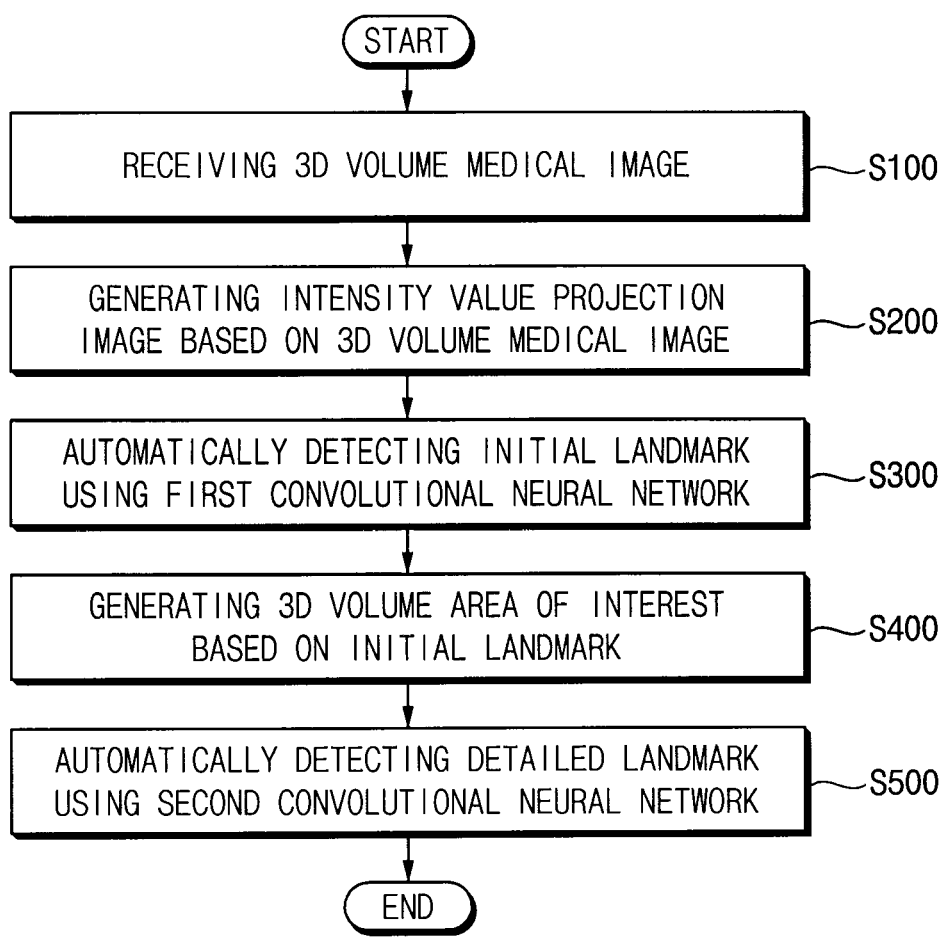

2D convolution on an image 3D convolution on a volume

METHOD AND APPARATUS FOR AUTOMATED DETECTION OF LANDMARKS FROM 3D MEDICAL IMAGE DATA BASED ON DEEP LEARNING

TECHNICAL FIELD

The present inventive concept relates to a method and an apparatus for automated detection of landmarks from 3D medical image data. More particularly, the present inventive concept relates to a method and an apparatus for automated detection of landmarks from 3D medical image data using deep learning.

BACKGROUND

Computed Tomography (CT), Cone-beam CT (CBCT) and Magnetic Resonance Imaging (MRI) images acquired to diagnose a patient's head, neck and mouth in dentistry, oral and maxillofacial surgery, and plastic surgery are 3D volume data in which hundreds of 2D slide images are accumulated.

In order to establish a diagnosis and treatment plan, or to compare before/after treatment, a process of analyzing the 3D volume data must be performed. This analysis process includes marking the patient's anatomical landmarks from 3D volume data and measures the distance, ratio, and angle using the landmarks. However, manually specifying and marking a point in a 3D space from the 3D volume data including hundreds of slide images is a difficult and time-consuming task. Thus, a method for automated detection of the landmarks from the 3D volume data is needed.

Due to this need, methods for automated detection or analysis of the patient's anatomical landmarks have been proposed. An automatic method for detecting landmarks from 2D images (X-ray images), not 3D volume data, has been proposed. A method for detecting and analyzing landmarks from 3D volume data through user interaction has been proposed. An automatic method for detecting the landmarks from a 2D projection image, which is generated by extracting a 3D facial bone model from 3D volume data and projecting the extracted 3D facial bone model in two dimensions, has been proposed.

However, as in the present inventive concept, no method for automatic detecting from 3D volume data has been proposed. In the automatic method for detecting the landmarks from the 2D projection image which has the highest correlation with the present inventive concept, the accuracy of automatic detection is affected by a quality of the extracted 3D facial bone model.

DETAILED EXPLANATION OF THE INVENTION

Technical Purpose

The purpose of the present inventive concept is providing a method for automated detection of landmarks from 3D medical image data using deep learning, capable of automatically detecting the patient's anatomical landmarks by using the 3D volume data itself without a user input or an additional 3D model extracting process.

Another purpose of the present inventive concept is providing an apparatus operating the method for automated detection of landmarks from 3D medical image data using deep learning.

Technical Solution

In an embodiment of a method for automated detection of landmarks from 3D medical image data using deep learning according to the present inventive concept, the method includes receiving a 3D volume medical image, generating a 2D intensity value projection image based on the 3D volume medical image, automatically detecting an initial anatomical landmark using a first convolutional neural network based on the 2D intensity value projection image, generating a 3D volume area of interest based on the initial anatomical landmark and automatically detecting a detailed anatomical landmark using a second convolutional neural network different from the first convolutional neural network based on the 3D volume area of interest.

In an embodiment of the present inventive concept, the 2D intensity value projection image may be generated by projecting intensity values of the 3D volume medical image in one direction.

In an embodiment of the present inventive concept, a standard deviation of the intensity values of the 3D volume medical image may be calculated in one direction to generate the 2D intensity value projection image.

In an embodiment of the present inventive concept, the 2D intensity value projection image may include a front intensity value projection image and a side intensity value projection image.

In an embodiment of the present inventive concept, the automatically detecting the initial anatomical landmark may include passing the front intensity value projection image and the side intensity value projection image through the first convolutional neural network.

In an embodiment of the present inventive concept, the automatically detecting the initial anatomical landmark may include detecting a front initial anatomical landmark based on the front intensity value projection image, detecting a side initial anatomical landmark based on the side intensity value projection image and determining the initial anatomical landmark by combining the front initial anatomical landmark and the side initial anatomical landmark.

In an embodiment of the present inventive concept, the first convolutional neural network may be a 2D fully convolutional deep neural network configured to output a 2D output based on a 2D input. The second convolutional neural network is a 3D fully convolutional deep neural network configured to output a 3D output based on a 3D input.

In an embodiment of the present inventive concept, an input data of the first convolutional neural network may be the 2D intensity value projection image and an output data of the first convolutional neural network may include a temporary initial anatomical landmark. The output data of the first convolutional neural network may be a 2D image having a greatest value at a position corresponding to the temporary initial anatomical landmark. An input data of the second convolutional neural network may be the 3D volume area of interest and an output data of the second convolutional neural network may include a temporary detailed anatomical landmark. The output data of the second convolutional neural network may be a 3D volume image having a greatest value at a position corresponding to the temporary detailed anatomical landmark.

In an embodiment of the present inventive concept, the generating the 3D volume area of interest may include extending from coordinates of the initial anatomical landmark in an x-axis direction, a y-axis direction, and a z-axis direction, respectively. A central point of the 3D volume area of interest may have the coordinates of the initial anatomical landmark.

In an embodiment of the present inventive concept, the detailed anatomical landmark may include first detailed landmarks disposed on a surface of a maxillofacial bone.

In an embodiment of the present inventive concept, the first detailed landmarks may include Nasion, Anterior Nasal Spine, Point-A, Posterior Nasal Spine, Point-B, Pogonion, Gnathion, Right/Left of Orbitale Superius, Right/Left of Orbitale Inferius, Right/Left of Sutura Zygomaticofrontale, Right/Left of Foramen Mentale, Basion, Right Porion, Right/Left of *Condylus Medialis*, Right/Left of *Condylus Lateralis*, Right/Left of Areus Zygomatieus, Right/Left of Inferior Gonion, Right/Left of Posterior Gonion and Right of Processus Coronoideus.

In an embodiment of the present inventive concept, the detailed anatomical landmark may include a second detailed landmark disposed in a middle of a craniomaxillofacial soft tissue area.

In an embodiment of the present inventive concept, the second detailed landmark may include Sella which is a central point of *Sella turcica*.

In an embodiment of the present inventive concept, the detailed anatomical landmark may include third detailed landmarks disposed on a maxillofacial skin surface.

In an embodiment of the present inventive concept, the third detailed landmark may include *Glabella*, Soft Tissue Nasion, Pronasale, Subnasale, Upper Lip Superior, Lower Lip Superior, Soft Tissue Pogonion, Soft Tissue Gnathion and Soft Tissue B-point.

In an embodiment of the present inventive concept, the detailed anatomical landmark may include fourth detailed landmarks related with teeth and disposed inside of a jawbone.

In an embodiment of the present inventive concept, the fourth detailed landmarks may include Central Incisor Root, First Molar Distal Root and Canine Root.

In an embodiment of the present inventive concept, the detailed anatomical landmark may include fifth detailed landmarks related with the teeth and disposed on the teeth.

In an embodiment of the present inventive concept, the fifth detailed landmarks may include Mid Point of Central Incisors, Distal Point of First Molar Crown, Cusp Tip and Distal Point of Canine Crown.

In an embodiment of an apparatus for automated detection of landmarks from 3D medical image data using deep learning according to the present inventive concept, the apparatus includes an intensity value projection image generator configured to receive a 3D volume medical image and to generate a 2D intensity value projection image based on the 3D volume medical image, an initial landmark automatic detector configured to automatically detect an initial anatomical landmark using a first convolutional neural network based on the 2D intensity value projection image, a 3D volume area of interest generator configured to receive the 3D volume medical image and to generate a 3D volume area of interest from the 3D volume medical image based on the initial anatomical landmark and a detailed landmark automatic detector configured to automatically detect a detailed anatomical landmark using a second convolutional neural network different from the first convolutional neural network based on the 3D volume area of interest.

In an embodiment of a non-transitory computer-readable recording medium according to the present inventive concept, the non-transitory computer-readable recording medium has recorded thereon at least one program comprising commands, which when executed by a computer, performs the method for automated detection of landmarks from 3D medical image data using deep learning.

Effect of the Invention

According to the method and the apparatus for automated detection of landmarks from 3D medical image data using deep learning of the present inventive concept, the deep learning model including 3D convolutional operation is employed so that the patient's anatomical landmarks may be automatically detected by using the 3D volume data itself without a user input or an additional 3D model extracting process.

Particularly, the anatomical 3D landmarks of a patient's oral and maxillofacial areas may be automatically detected in a short time and the patient's oral and maxillofacial areas may be easily measured and analyzed based on the automatically detected landmarks.

Extracting an accurate 3D model from the volume data with low image quality and high noise, such as CBCT, may be difficult so that it is difficult to apply the conventional method, in which the 3D model is projected into the 2D model, to the volume data with low image quality and high noise. Similarly, a metal noise may be frequently generated by dental prosthesis or orthodontic devices so that it is difficult to apply the conventional method for detecting teeth landmarks. In addition, anatomical landmarks which are not disposed on a bone surface or at boundaries of soft and hard tissues (e.g. *Sella turcica*'s central point or teeth root-related landmarks) are not disposed on a surface of the 3D model and accordingly are not automatically detected by the conventional method. In contrast, according to the present inventive concept, the landmarks may be accurately and automatically detected for the 3D volume data with low image quality and high noise. In addition, according to the present inventive concept, even if the metal noise is generated by dental prosthesis or orthodontic devices, the anatomical landmarks may be accurately and automatically detected. In addition, according to the present inventive concept, the anatomical landmarks which are not disposed on the bone surface or at boundaries of soft and hard tissues may be automatically detected.

BRIEF EXPLANATION OF THE DRAWINGS

FIG. 3 is a flowchart diagram illustrating the method for automated detection of landmarks from 3D medical image data using deep learning according to an embodiment of the present inventive concept.

BEST MODE FOR CARRYING OUT THE INVENTION

Figure 1:
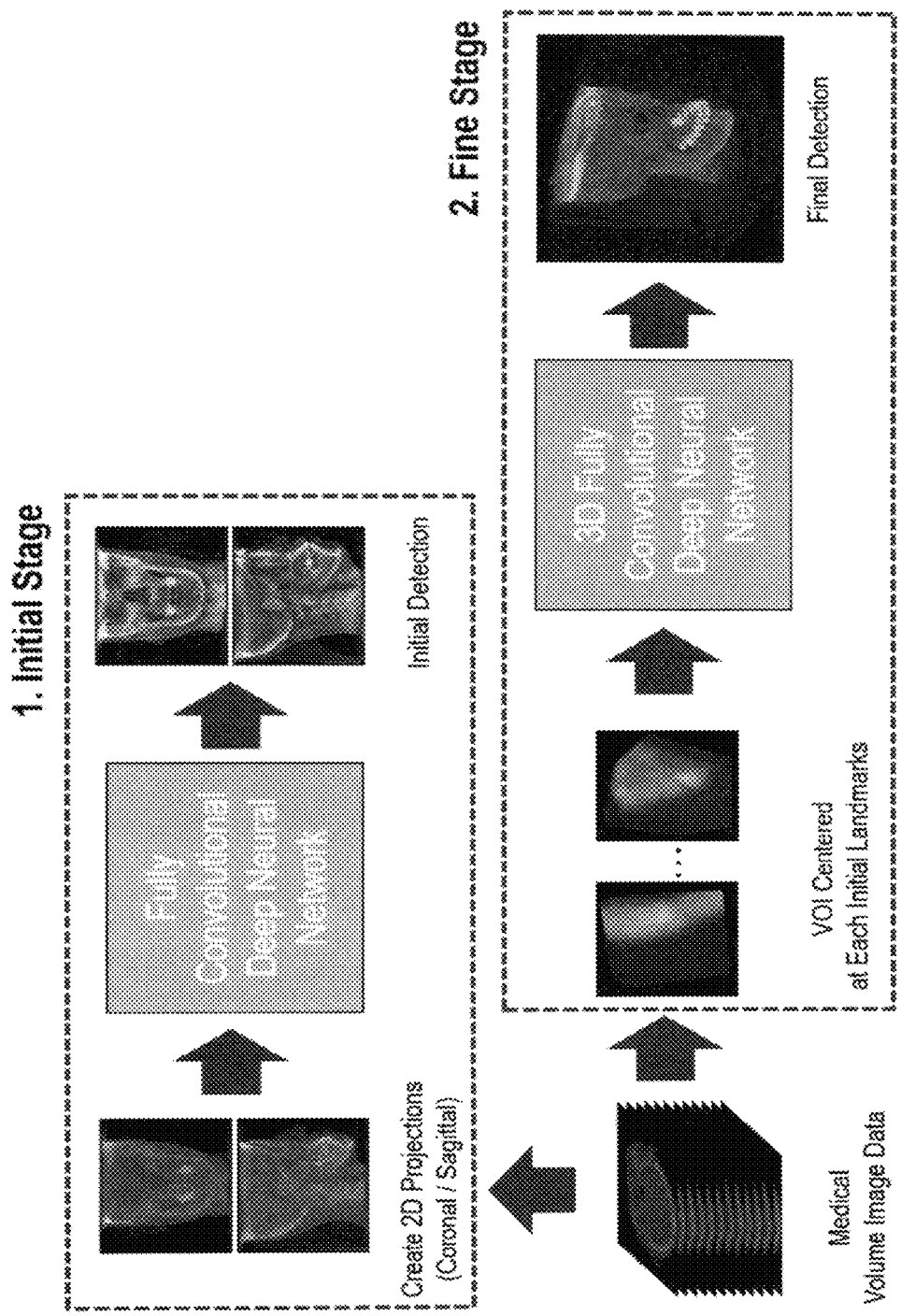
FIG. 1 illustrates a method for automated detection of landmarks from 3D medical image data using deep learning according to an embodiment of the present inventive concept.

The present inventive concept now will be described more fully hereinafter with reference to the accompanying drawings, in which exemplary embodiments of the present invention are shown. The present inventive concept may, however, be embodied in many different forms and should not be construed as limited to the exemplary embodiments set fourth herein.

Rather, these exemplary embodiments are provided so that this disclosure will be thorough and complete, and will fully convey the scope of the present invention to those skilled in the art.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

The terminology used herein is for the purpose of describing particular exemplary embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the inventive concept as used herein.

Hereinafter, preferred embodiments of the present inventive concept will be explained in detail with reference to the accompanying drawings. The same reference numerals are used for the same elements in the drawings, and duplicate explanations for the same elements may be omitted.

Figure 2:
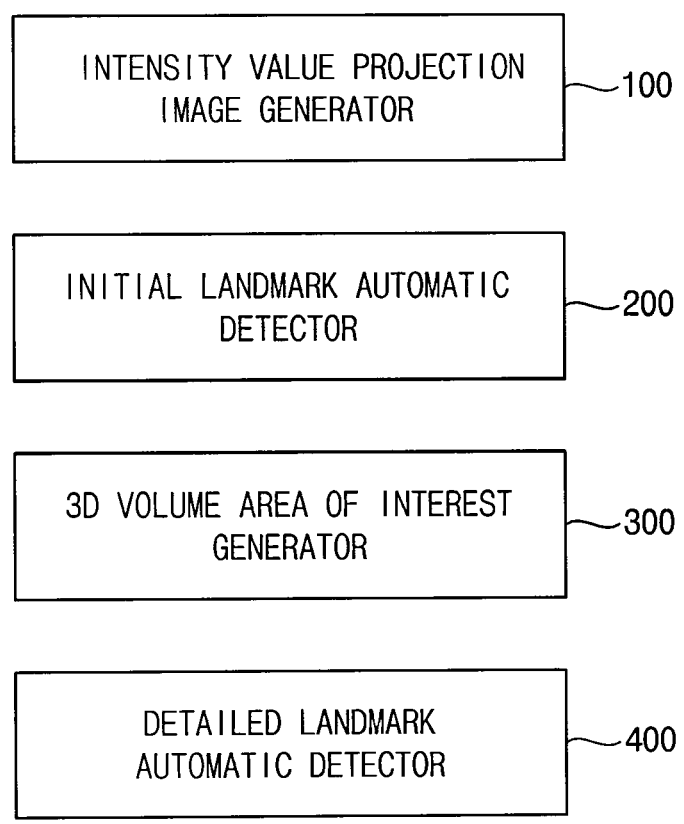
FIG. 2 is a block diagram illustrating an apparatus for automated detection of landmarks from 3D medical image data using deep learning according to an embodiment of the present inventive concept.
Figure 4A:
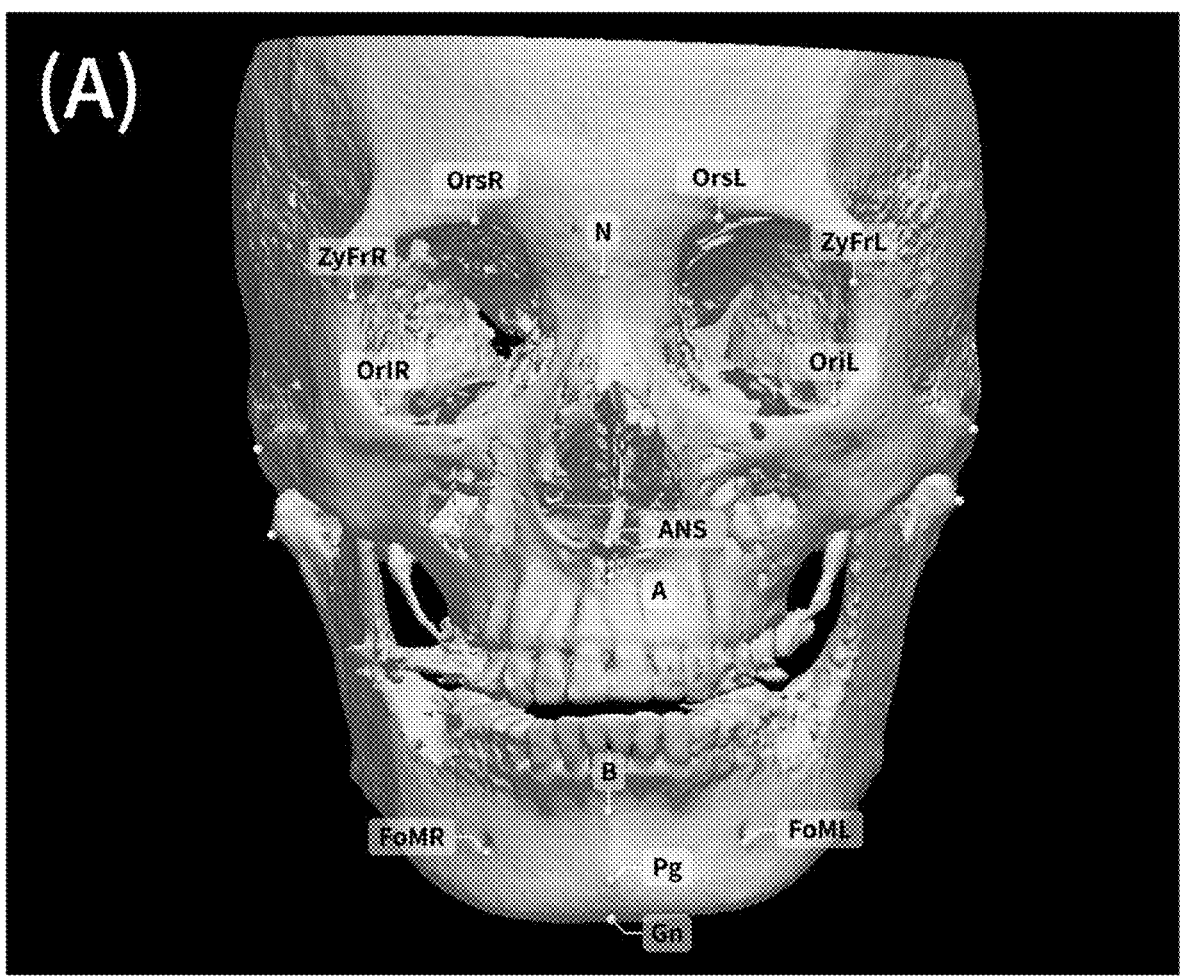
FIGS. 4a, 4b, 4c and 4d illustrate examples of detailed anatomical landmarks related with a maxillofacial bone detected by a detailed landmark automatic detector of FIG. 2.
Figure 4B:
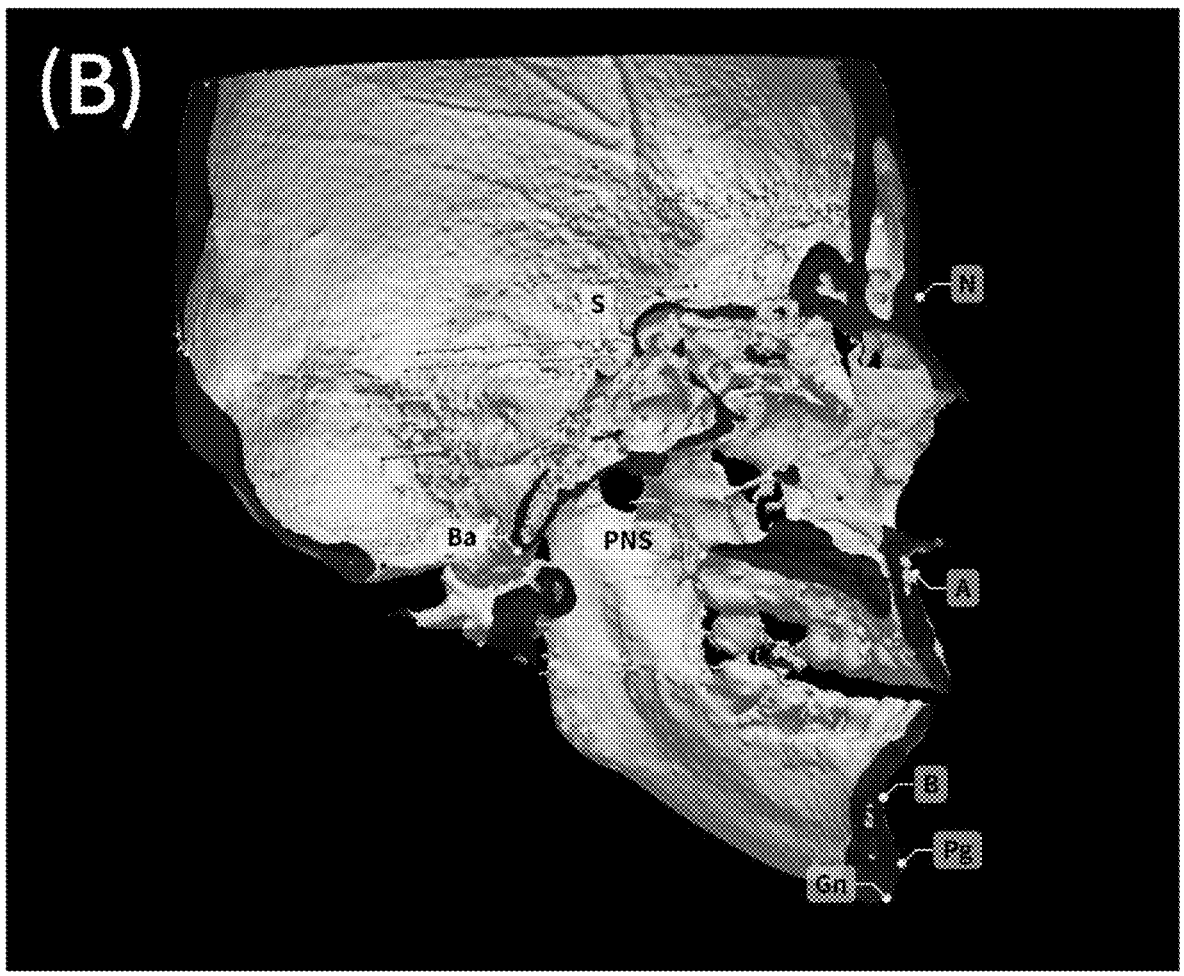
Figure 4C:
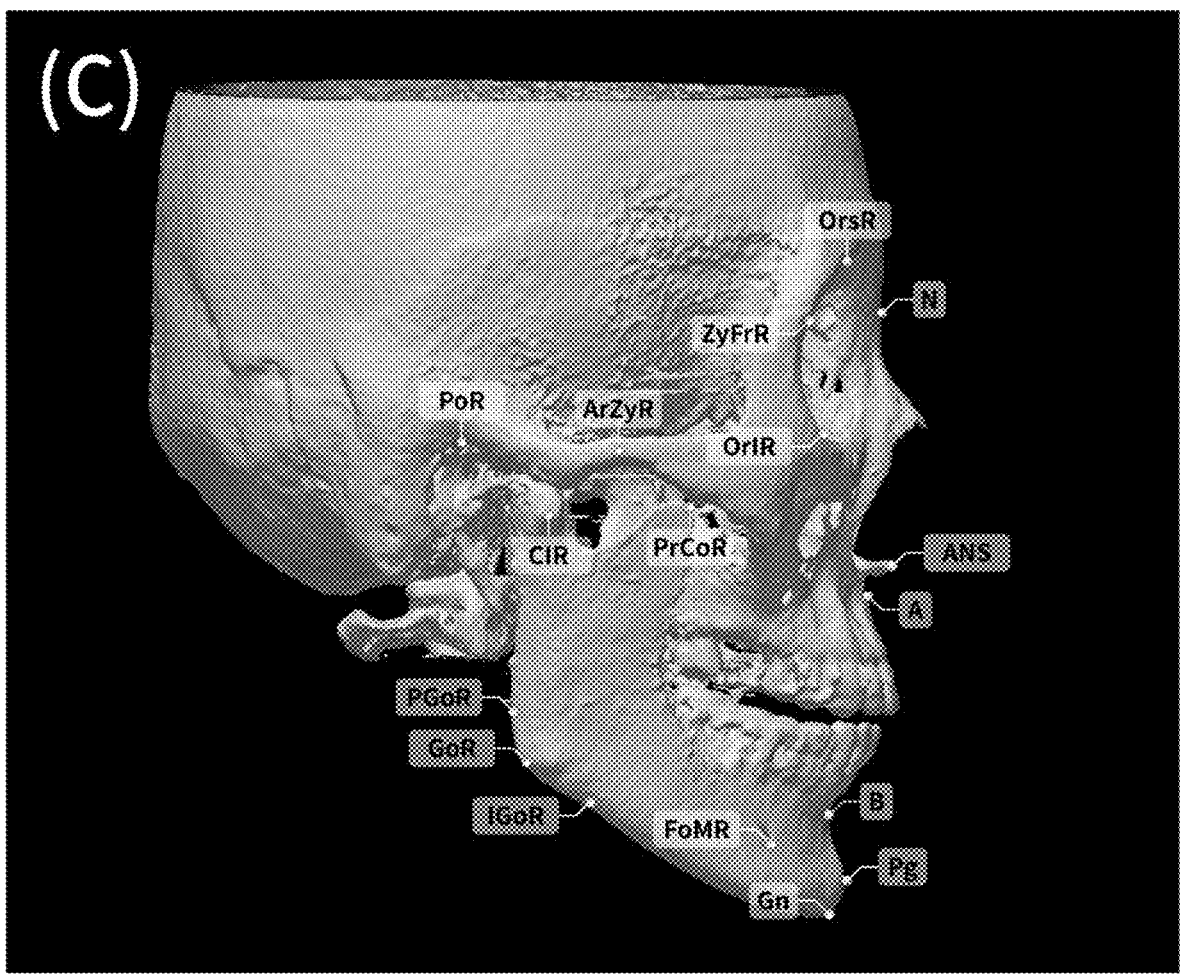
Figure 4D:
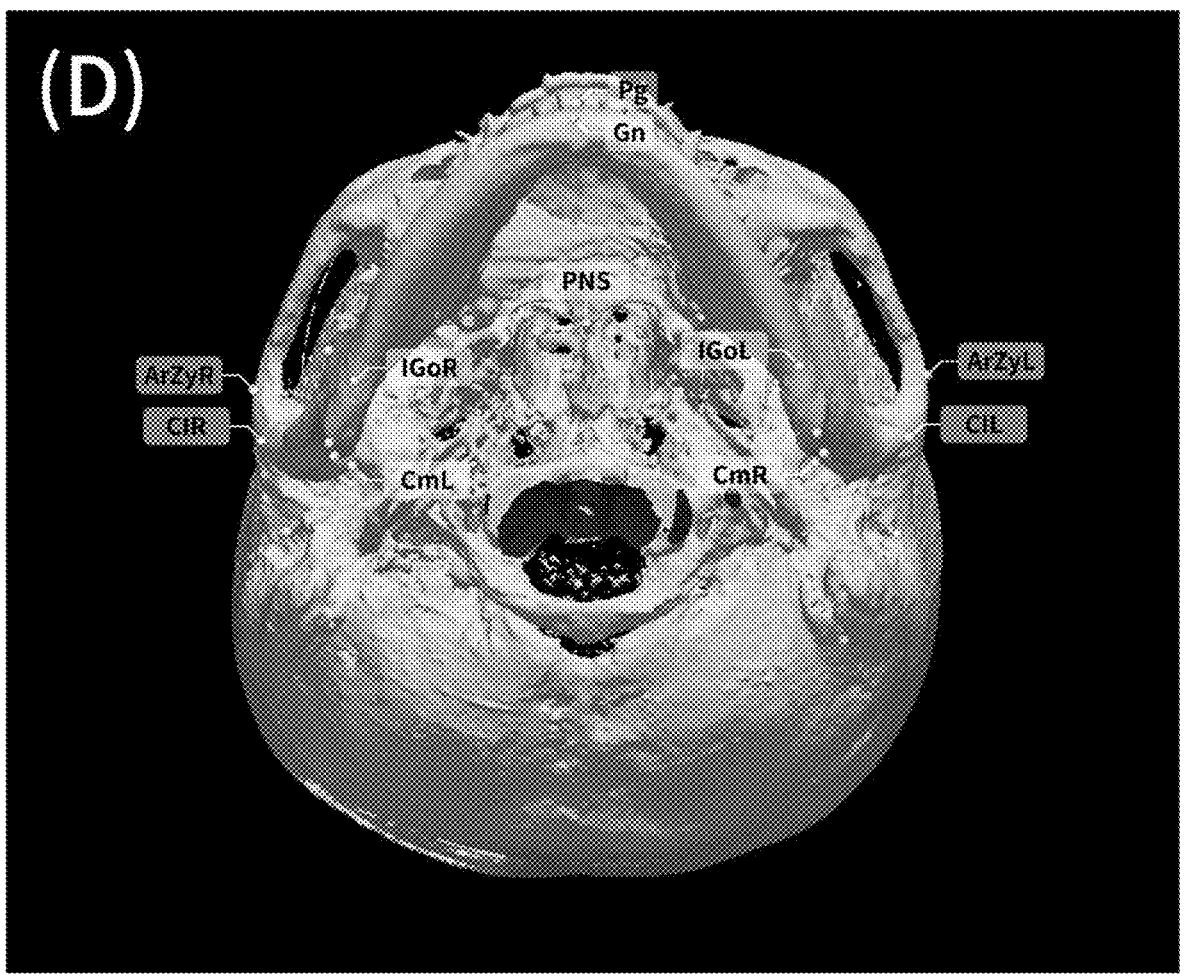

FIG. 1 illustrates a method for automated detection of landmarks from 3D medical image data using deep learning according to an embodiment of the present inventive concept. FIG. 2 is a block diagram illustrating an apparatus for automated detection of landmarks from 3D medical image data using deep learning according to an embodiment of the present inventive concept. FIG. 3 is a flowchart diagram illustrating the method for automated detection of landmarks from 3D medical image data using deep learning according to an embodiment of the present inventive concept.

Referring to FIGS. 1 to 3, the present invention briefly includes (1) an initial automatic detecting step (Initial Stage) and (2) a detailed automatic detecting step (Fine stage).

(1) the initial automatic detecting step includes a 3D volume data preprocessing step and an initial automatic landmark detecting step using a fully convolutional neural network deep learning model.

(2) the detailed automatic detecting step includes a 3D volume area of interest (VOI) automatic generating step using the initial automatic landmark detection result and a detailed automatic landmark detecting step using a 3D fully convolutional neural network deep learning model.

Herein, the 3D volume medical image data may be one of CT, CBCT, MM and PET (Positron Emission Tomography). In addition, the 3D volume medical image data may be any medical image data including the patient's anatomy as 3D volume data except for the CT, CBCT, MRI and PET.

The patient's anatomical landmark detected by the present inventive concept may be any landmark included in the 3D volume medical image data. In the present inventive concept, all target landmarks may be automatically detected by applying the same proposed method to the all target landmarks without separate processing.

In FIG. 2, the apparatus for automated detection of the landmarks from the 3D medical image data using deep learning includes an intensity value projection image generator 100, an initial landmark automatic detector 200, a 3D volume area of interest generator 300 and a detailed landmark automatic detector 400. The intensity value projection image generator 100 may receive a 3D volume medical image and generate a 2D intensity value projection image based on the 3D volume medical image. The initial landmark automatic detector 200 may automatically detect an initial anatomical landmark using a first convolutional neural network based on the 2D intensity value projection image. The 3D volume area of interest generator 300 may receive the 3D volume medical image and generate a 3D volume area of interest from the 3D volume medical image based on the initial anatomical landmark. The detailed landmark automatic detector 400 may automatically detect a detailed anatomical landmark using a second convolutional neural network different from the first convolutional neural network based on the 3D volume area of interest.

In FIG. 3, the method for automated detection of the landmarks from the 3D medical image data using deep learning may include a step S100 of receiving the 3D volume medical image, a step S200 of generating the 2D intensity value projection image based on the 3D volume medical image, a step S300 of automatically detecting the initial anatomical landmark using the first convolutional neural network based on the 2D intensity value projection image, a step S400 of generating the 3D volume area of interest based on the initial anatomical landmark and a step S500 of automatically detecting the detailed anatomical landmark using the second convolutional neural network different from the first convolutional neural network based on the 3D volume area of interest.

FIGS. 4a, 4b, 4c and 4d illustrate examples of detailed anatomical landmarks related with a maxillofacial bone detected by the detailed landmark automatic detector 400 of FIG. 2.

Referring to FIGS. 1 to 4d, the detailed anatomical landmarks detected by the detailed landmark automatic detector 400 may include first detailed landmarks disposed on a surface of the maxillofacial bone.

As shown in FIGS. 4a to 4d, the first detailed landmarks may include Nasion (N), Anterior Nasal Spine (ANS), Point-A (A), Posterior Nasal Spine (PNS), Point-B (B), Pogonion, Gnathion (Pg), Right/Left of Orbitale Superius (OrSR/OrSL), Right/Left of Orbitale Inferius (OriR/OriL), Right/Left of Sutura Zygomaticofrontale (ZyFrR/ZyFrL), Right/Left of Foramen Mentale (FoMR/FoML), Basion (Ba), Right Porion (PoR), Right/Left of *Condylus Medialis* (CmR/CmL), Right/Left of *Condylus Lateralis* (ClR/ClL), Right/Left of Areus Zygomatieus (ArZyR/ArZyL), Right/Left of Inferior Gonion (IGoR/IgoL), Right/Left of Posterior Gonion (PgoR/PgoL) and Right of Processus Coronoideus (PrCor).

The detailed anatomical landmarks detected by the detailed landmark automatic detector 400 may include a second detailed landmark disposed in the middle of a craniomaxillofacial soft tissue area. As shown in FIGS. 4a to 4d, the second detailed landmark may include *Sella* (S) which is a central point of *Sella turcica*.

According to the present embodiment, the second detailed landmark disposed not on the bone surface but in the middle of the soft tissue may also be accurately detected.

Figure 5:
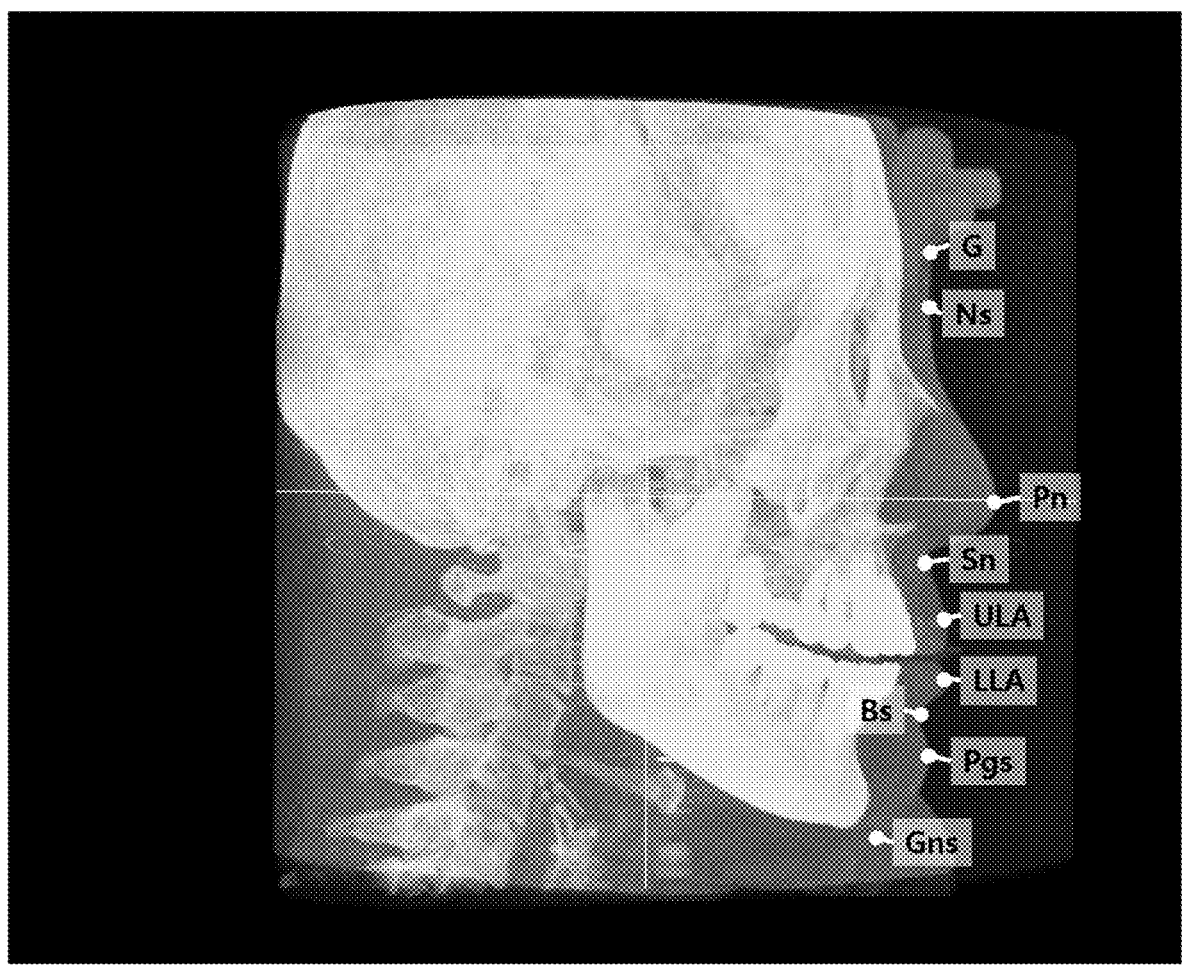
FIG. 5 illustrates examples of detailed anatomical landmarks disposed on a skin surface detected by the detailed landmark automatic detector of FIG. 2.

FIG. 5 illustrates examples of detailed anatomical landmarks disposed on a skin surface detected by the detailed landmark automatic detector 400 of FIG. 2.

Referring to FIGS. 1 to 5, the detailed anatomical landmarks detected by the detailed landmark automatic detector 400 may include third detailed landmarks disposed on a maxillofacial skin surface.

As shown in FIG. 5, the third detailed landmarks may include *Glabella* (G), Soft Tissue Nasion (Ns), Pronasale (Pn), Subnasale (Sn), Upper Lip Superior (ULA), Lower Lip Superior (LLA), Soft Tissue Pogonion (Pgs), Soft Tissue Gnathion (Gns) and Soft Tissue B-point (Bs).

According to the present embodiment, the third detailed landmarks disposed not on the bone surface but on the skin surface may also be accurately detected.

Figure 6A:
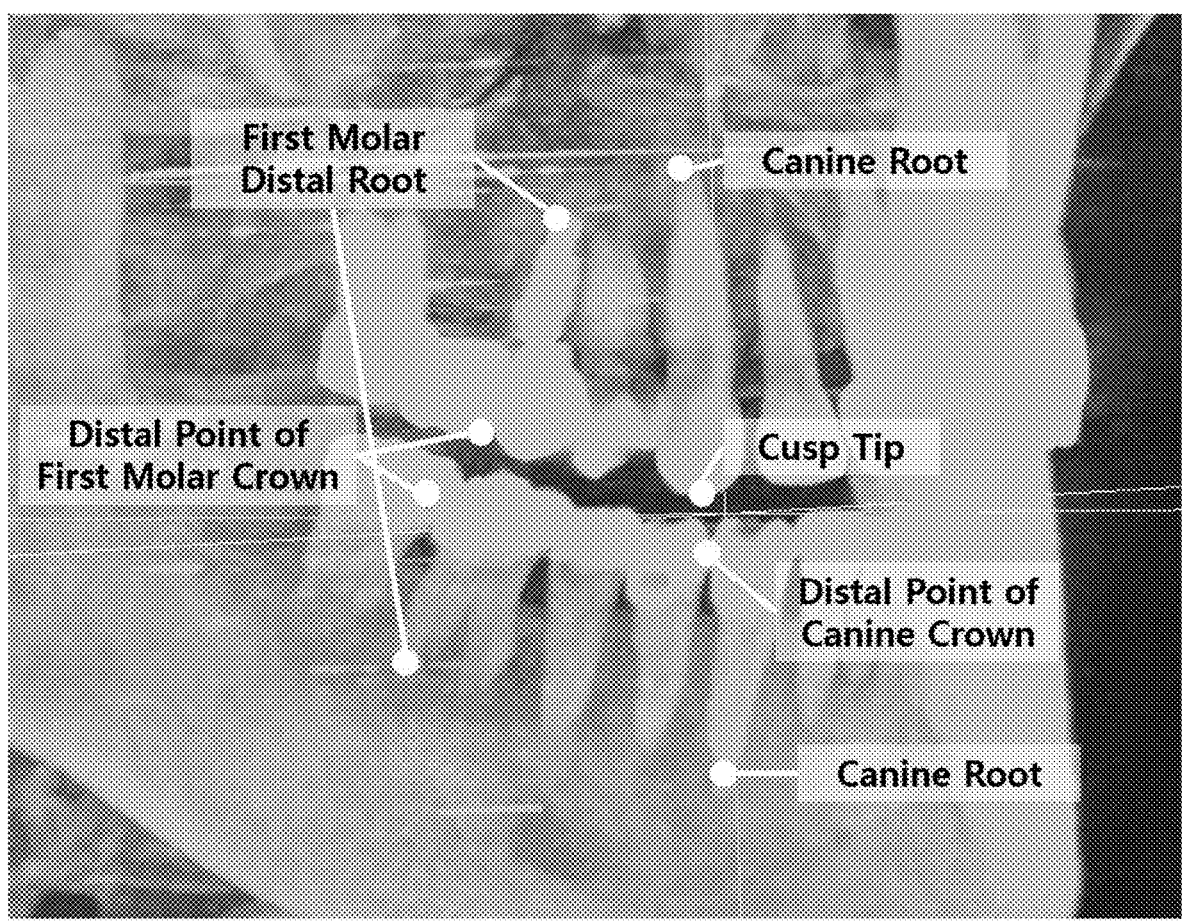
FIGS. 6a and 6b illustrate examples of detailed anatomical landmarks related with teeth detected by the detailed landmark automatic detector of FIG. 2.
Figure 6B:
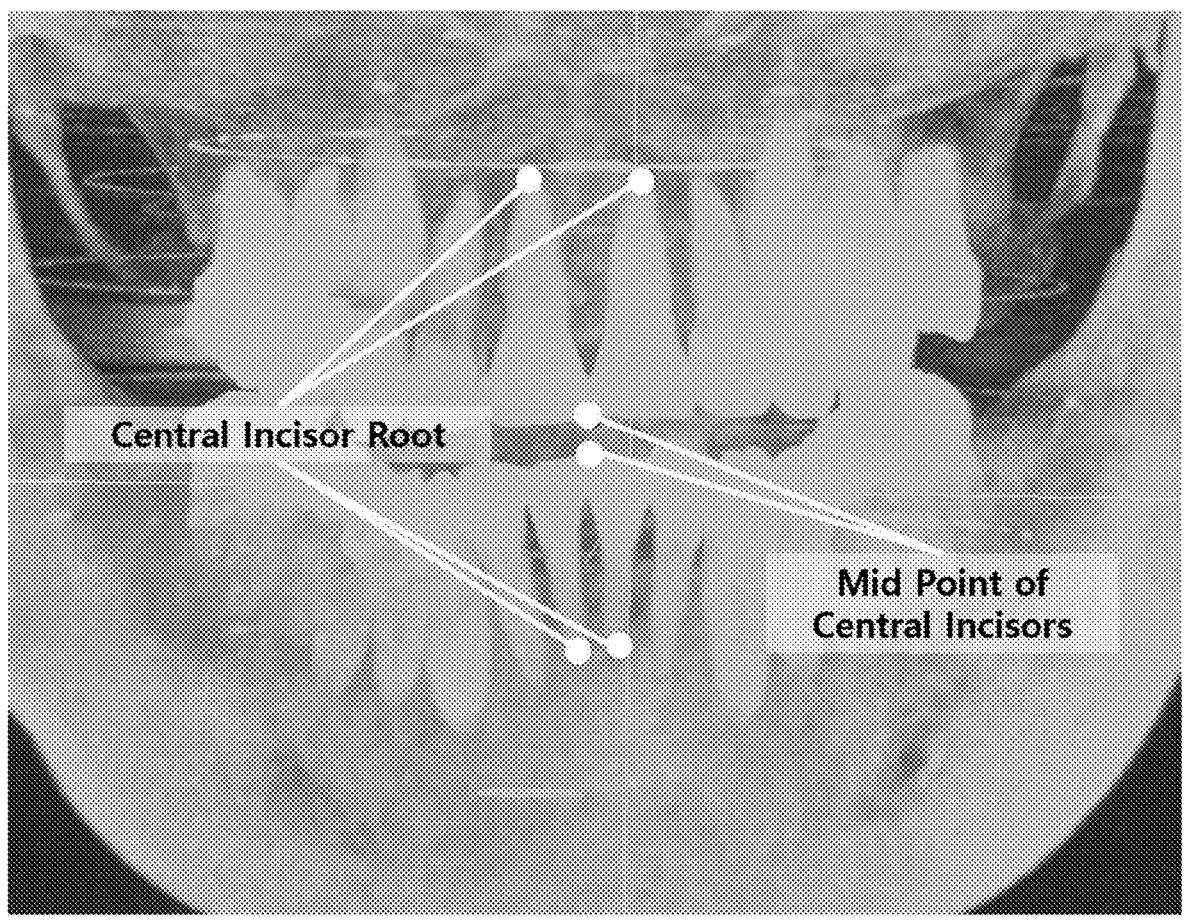

FIGS. 6a and 6b illustrate examples of detailed anatomical landmarks related with teeth detected by the detailed landmark automatic detector of FIG. 2.

Referring to FIGS. 1 to 6b, the detailed anatomical landmarks detected by the detailed landmark automatic detector 400 may include fourth detailed landmarks related with the teeth and disposed inside of a jawbone.

As shown in FIGS. 6a and 6b, the fourth detailed landmarks may include Central Incisor Root, First Molar Distal Root and Canine Root.

The detailed anatomical landmarks detected by the detailed landmark automatic detector 400 may include fifth detailed landmarks related with the teeth and disposed on the teeth.

As shown in FIGS. 6a and 6b, the fifth detailed landmarks may include Mid Point of Central Incisors, Distal Point of First Molar Crown, Cusp Tip and Distal Point of Canine Crown.

According to the present embodiment, the fourth detailed landmarks disposed not on the bone surface but on the skin surface and the fifth detailed landmarks disposed on the teeth may also be accurately detected.

Figure 7:
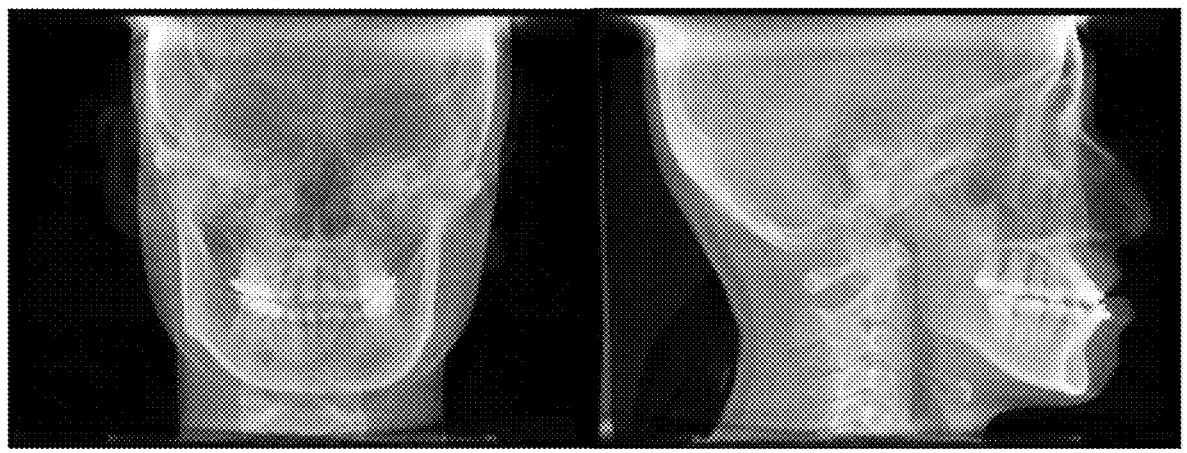
FIG. 7 illustrates an example of an intensity value projection image generated by an intensity value projection image generator of FIG. 2.

FIG. 7 illustrates an example of the intensity value projection image generated by the intensity value projection image generator 100 of FIG. 2.

Referring to FIGS. 1 to 7, the initial landmarks may be automatically detected for an entire area of the 3D volume medical image data in (1) the initial automatic detecting step. Prior to the initial automatic detection, the 3D volume data may be processed to correspond to the fully convolutional neural network deep learning model. This process may be called to preprocessing. The intensity value projection image generator 100 may operate the preprocessing.

The preprocessing may be image processing respectively generating an intensity value projection image in a front direction (a coronal view) and an intensity value projection image in a lateral direction (a sagittal view) using the intensity values of the 3D volume medical image data. In the preprocessing, the intensity value may be scanned in each projection direction and the intensity value may be reflected in a final projection image according to a projection method.

The intensity value projection image generator 100 may receive the 3D volume medical image and generate a 2D intensity value projection image based on the 3D volume medical image.

The 2D intensity value projection image is generated by projecting intensity values of the 3D volume medical image in one direction. For example, a standard deviation of the intensity values of the 3D volume medical image may be calculated in one direction to generate the 2D intensity value projection image. Alternatively, the intensity value projection image generator 100 may generate the 2D intensity value projection image using a maximum value of the intensity values of the 3D volume medical image, a minimum value of the intensity values of the 3D volume medical image, an average value of the intensity values of the 3D volume medical image or a median value of the intensity values of the 3D volume medical image.

As shown in FIG. 7, the 2D intensity value projection image may include a front intensity value projection image (a left portion of FIG. 7) and a side intensity value projection image (a right portion of FIG. 7).

Herein, the initial landmark automatic detector 200 respectively learns and uses a deep learning model having the same structure for the front intensity value projection image and the side intensity value projection image. The initial landmark automatic detector 200 may pass the front intensity value projection image and the side intensity value projection image through the first convolutional neural network.

Figure 8:
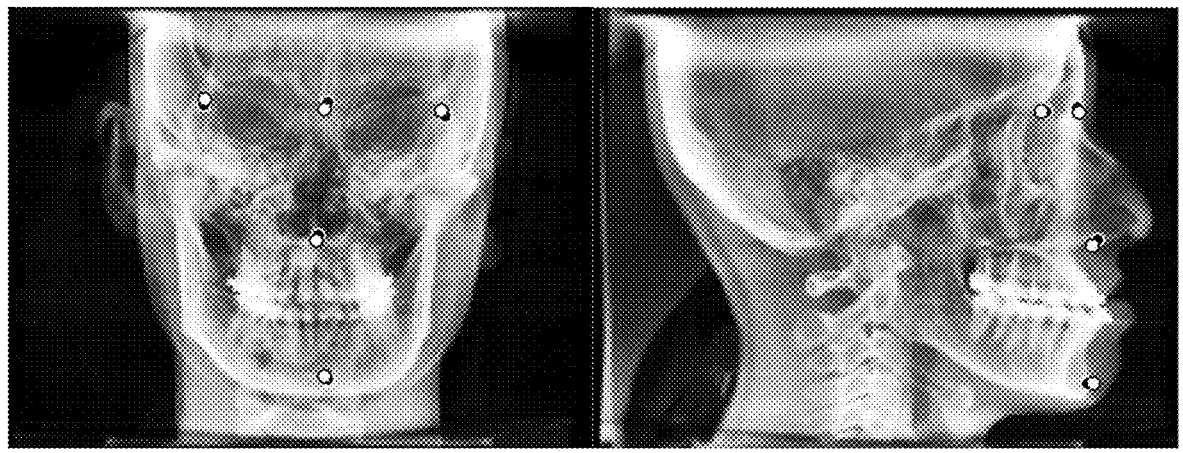
FIG. 8 illustrates examples of initial anatomical landmarks detected by an initial landmark automatic detector of FIG. 2.

FIG. 8 illustrates examples of initial anatomical landmarks detected by the initial landmark automatic detector 200 of FIG. 2.

Referring to FIGS. 1 to 8, the initial landmark automatic detector 200 may automatically detect the initial anatomical landmarks using the first convolutional neural network based on the 2D intensity value projection image.

The 2D intensity value projection image is generated in the preprocessing. The 2D intensity value projection image is used as an input image, and a learning process is performed in which the fully convolutional neural network deep learning model automatically detects the landmarks in the projection image. The fully convolutional neural network deep learning model may be a neural network deep learning model including convolutional layers.

FIG. 8 represents an example of an initial landmark detection result automatically detected by the fully convolutional neural network deep learning model in which training has been completed using the projection image in each direction (e.g. the coronal view and the sagittal view). A left portion of FIG. 8 represents a result of the front intensity value projection image (the coronal view), a right portion of FIG. 8 represents a result of the side intensity value projection image (the sagittal view), black dots in FIG. 8 represent positions of landmarks of ground truths used in training and white dots in FIG. 8 represent positions of the initial landmarks automatically detected by the fully convolutional neural network deep learning model.

For example, the initial landmark automatic detector 200 may convert 2D initial landmarks into 3D initial landmarks. The initial landmark automatic detector 200 may detect front initial anatomical landmarks based on the front intensity value projection image and side initial anatomical landmarks based on the side intensity value projection image. The initial landmark automatic detector 200 may determine the initial anatomical landmarks by combining the front initial anatomical landmarks and the side initial anatomical landmarks.

Figure 9:
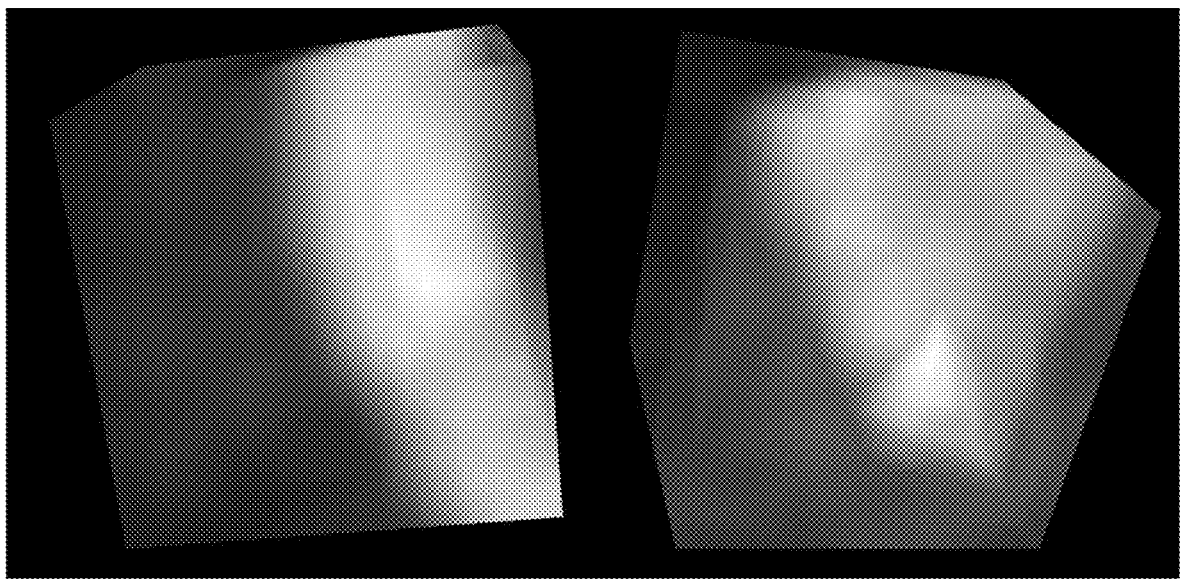
FIG. 9 illustrates an example of a 3D volume area of interest generated by a 3D volume area of interest generator of FIG. 2.

FIG. 9 illustrates an example of the 3D volume area of interest generated by the 3D volume area of interest generator 300 of FIG. 2.

Referring to FIGS. 1 to 9, the 3D volume area of interest generator 300 may generate the 3D volume area of interest (VOI) based on the initial anatomical landmarks.

In (2) the detailed automatic detecting step, landmarks are detected in a detailed area using the initial automatic landmark detection result of (1) the initial automatic detecting step. First, the 3D volume area of interest (VOI) may be automatically extracted from an original 3D volume medical image data using the initial automatic landmark detection result. Each central point of each 3D volume area of interest (VOI) may be each initial landmark. Each 3D volume area of interest (VOI) may include a 3D volume area including a predetermined region centered on each initial landmark. The 3D volume area of interest (VOI) may have a form of a cube.

A left portion of FIG. 9 may represent a 3D volume area of interest for a first initial landmark and a right portion of FIG. 9 may represent a 3D volume area of interest for a second initial landmark different from the first initial landmark.

In this manner, the number of the 3D volume areas of interest may be the same as the number of the initial anatomical landmarks.

For example, the 3D volume area of interest generator 300 may generate the 3D volume area of interest (VOI) by extending from the coordinates of the initial anatomical landmark in an x-axis direction, a y-axis direction, and a z-axis direction, respectively. Herein, the central point of the 3D volume area of interest (VOI) may have the coordinates of the initial anatomical landmark.

For example, when the 3D volume area of interest (VOI) having a size of 10×10×10 is generated using the initial anatomical landmark, the coordinates of the initial anatomical landmark in the 3D volume area of interest (VOI) may be (5, 5, 5).

The detailed landmark automatic detector 400 may automatically detect the detailed anatomical landmark using the second convolutional neural network based on the 3D volume area of interest (VOI). The coordinate of the detailed anatomical landmark generated through the second convolutional neural network may not be (5, 5, 5) in the 3D volume area of interest (VOI). For example, if the coordinates of the detailed anatomical landmark generated through the second convolutional neural network are (5, 6, 7), it means that the location of the detailed landmark is moved by 1 in the y-axis and 2 in the z-axis compared to the initial landmark.

In the present embodiment, the 3D volume area of interest generator 300 may generate the 3D volume area of interest (VOI) based on the initial anatomical landmark and the detailed landmark automatic detector 400 only passes the 3D volume area of interest (VOI) through the second convolutional neural network. Thus, the amount of computation may be greatly reduced compared to the case where the 3D volume medical image is passed through the second convolutional neural network as it is and the accuracy of detecting the detailed landmark may be enhanced.

Figure 10A:
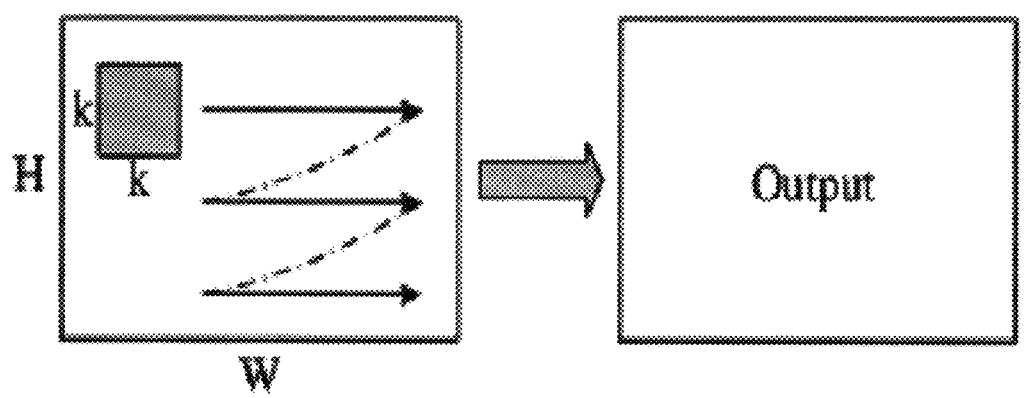
FIG. 10a illustrates convolution operations of a first convolutional neural network used in the initial landmark automatic detector of FIG. 2.
Figure 10B:
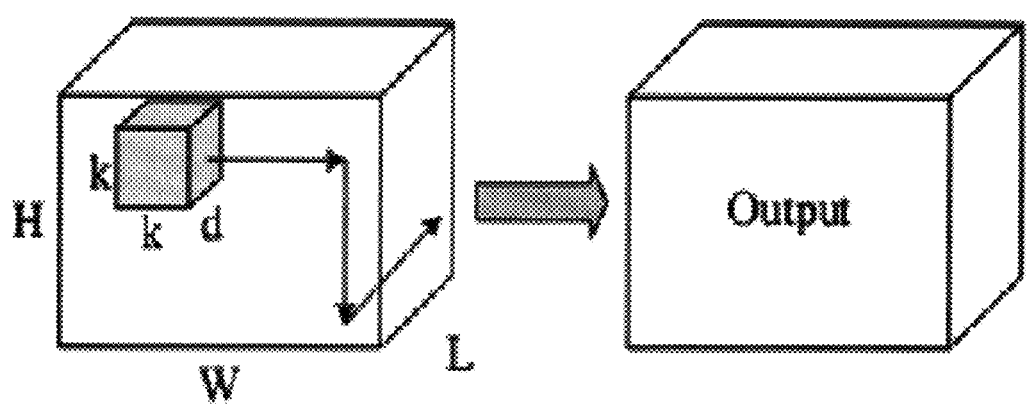
FIG. 10b illustrates convolution operations of a second convolutional neural network used in the detailed landmark automatic detector of FIG. 2.

FIG. 10*a* illustrates convolution operations of the first convolutional neural network used in the initial landmark automatic detector 200 of FIG. 2. FIG. 10*b* illustrates convolution operations of the second convolutional neural network used in the detailed landmark automatic detector 400 of FIG. 2.

Referring to FIGS. 1 to 10*b*, the first convolutional neural network used in the initial landmark automatic detector 200 may be different from the second convolutional neural network used in the detailed landmark automatic detector 400.

The first convolutional neural network is a 2D fully convolutional deep neural network that outputs a 2D output based on a 2D input. The second convolutional neural network is a 3D fully convolutional deep neural network that outputs a 3D output based on a 3D input. The fully convolutional neural network may mean a deep neural network in which all operations are composed only of convolutional operations.

In FIG. 10*a*, H represents a height of the 2D input, W represents a width of the 2D input, k represents a height and a width of a kernel and d represents a length of the kernel.

As explained above, the input data of the first convolutional neural network is the 2D intensity value projection image (e.g. the front intensity value projection image and the side intensity value projection image), the output data of the first convolutional neural network may include a temporary initial anatomical landmark and the output data of the first convolutional neural network may be a 2D image having the greatest value at a position corresponding to the temporary initial anatomical landmark.

The initial landmark automatic detector 200 may generate the anatomical initial landmark by converting the temporary initial anatomical landmark into 3D.

The input data of the second convolutional neural network is the 3D volume area of interest (VOI) and the output data of the second convolutional neural network may include a temporary detailed anatomical landmark and the output data of the second convolutional neural network may be a 3D volume image having the greatest value at a position corresponding to the temporary detailed anatomical landmark.

Figure 11:
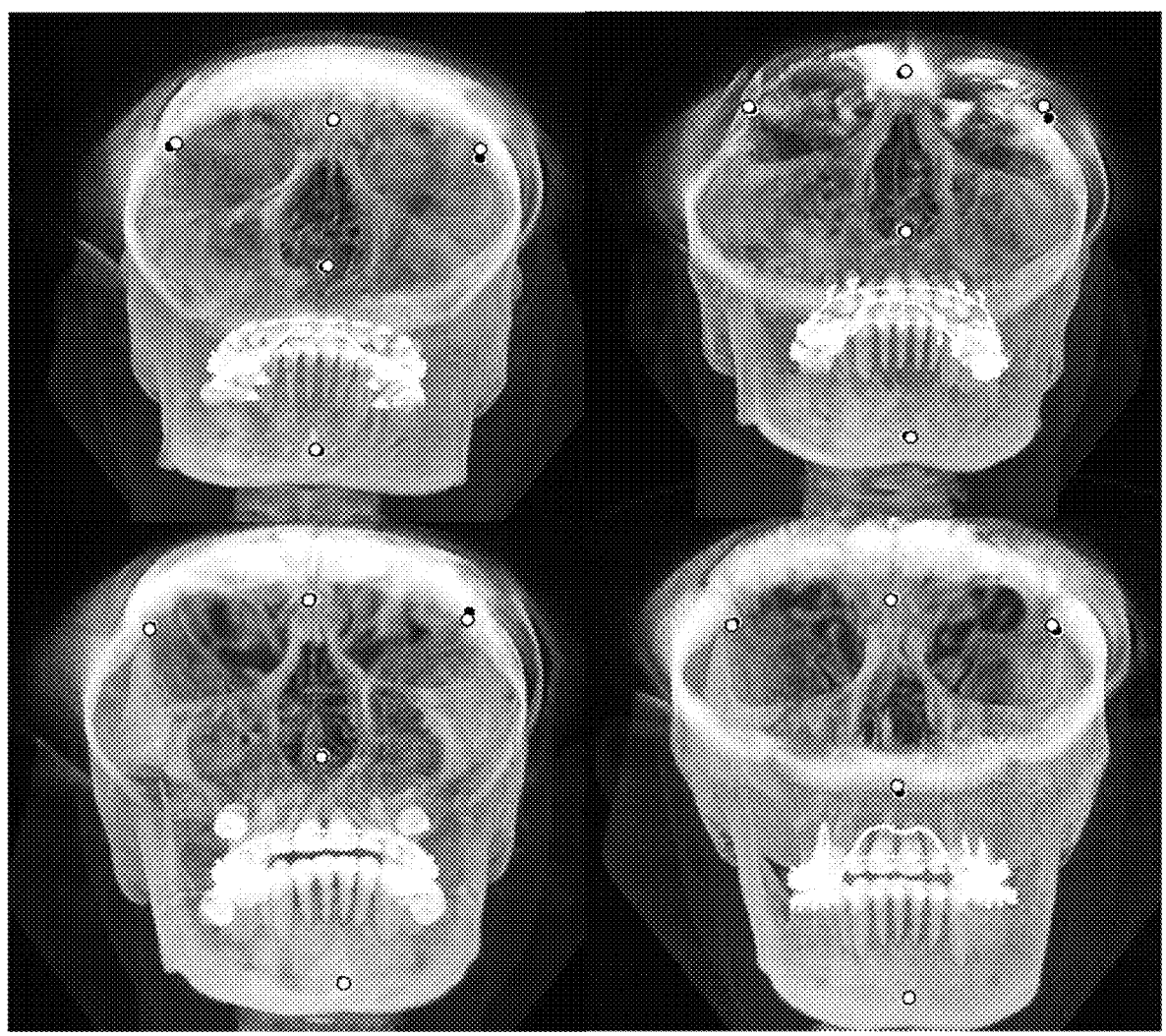
FIG. 11 illustrates detailed anatomical landmarks detected by the detailed landmark automatic detector of FIG. 2.

The detailed landmark automatic detector 400 may finally detect the anatomical detailed landmark by converting the temporary detailed anatomical landmark into coordinates in the 3D volume medical image FIG. 11 illustrates detailed anatomical landmarks detected by the detailed landmark automatic detector 400 of FIG. 2.

Referring to FIGS. 1 to 11, the 3D volume area of interest (VOI) data are used as an input image, and a learning process is performed in which the 3D fully convolutional neural network deep learning model automatically detects the 3D landmarks in the 3D volume area of interest (VOI) in detail. The 3D fully convolutional neural network deep learning model may be a neural network deep learning model including 3D convolutional layers.

Herein, one deep learning model may be trained and used for the 3D volume areas of interest (VOIs) of the different landmarks. FIG. 11 shows an example of a result of final landmarks automatically detected in detail in the original 3D volume medical image data using the learned deep learning model.

Black dots in FIG. 11 represent positions of landmarks of ground truths used in training and white dots in FIG. 11 represent positions of the detailed landmarks automatically detected by the 3D fully convolutional neural network deep learning model.

According to the present embodiment, the deep learning model including 3D convolutional operation is employed so that the patient's anatomical landmarks may be automatically detected by using the 3D volume data itself without a user input or an additional 3D model extracting process.

Particularly, the anatomical 3D landmarks of a patient's oral and maxillofacial areas may be automatically detected in a short time and the patient's oral and maxillofacial areas may be easily measured and analyzed based on the automatically detected landmarks.

Extracting an accurate 3D model from the volume data with low image quality and high noise, such as CBCT, may be difficult so that it is difficult to apply the conventional method, in which the 3D model is projected into the 2D model, to the volume data with low image quality and high noise. Similarly, a metal noise may be frequently generated by dental prosthesis or orthodontic devices so that it is difficult to apply the conventional method for detecting teeth landmarks. In addition, anatomical landmarks which are not disposed on a bone surface or at boundaries of soft and hard tissues (e.g. *Sella turcica*'s central point or teeth root-related landmarks) are not disposed on a surface of the 3D model and accordingly are not automatically detected by the conventional method. In contrast, according to the present inventive concept, the landmarks may be accurately and automatically detected for the 3D volume data with low image quality and high noise. In addition, according to the present inventive concept, even if the metal noise is generated by dental prosthesis or orthodontic devices, the anatomical landmarks may be accurately and automatically detected. In addition, according to the present inventive concept, the anatomical landmarks which are not disposed on the bone surface or at boundaries of soft and hard tissues may be automatically detected.

According to an embodiment of the present inventive concept, a non-transitory computer-readable storage medium having stored thereon program instructions of the above mentioned method for automated detection of landmarks from 3D medical image data may be provided. The above mentioned method may be written as a program executed on the computer. The method may be implemented in a general purpose digital computer which operates the program using a computer-readable medium. In addition, the structure of the data used in the above mentioned method may be written on a computer readable medium through various means. The computer readable medium may include program instructions, data files and data structures alone or in combination. The program instructions written on the medium may be specially designed and configured for the present inventive concept, or may be generally known to a person skilled in the computer software field. For example, the computer readable medium may include a magnetic medium such as a hard disk, a floppy disk and a magnetic tape, an optical recording medium such as CD-ROM and DVD, a magneto-optical medium such as floptic disc and a hardware device specially configured to store and execute the program instructions such as ROM, RAM and a flash memory. For example, the program instructions may include a machine language codes produced by a compiler and high-level language codes which may be executed by a computer using an interpreter or the like. The hardware device may be configured to operate as one or more software modules to perform the operations of the present inventive concept.

In addition, the above mentioned method for automated detection of landmarks from 3D medical image data may be implemented in a form of a computer-executed computer program or an application which are stored in a storage method.

INDUSTRIAL AVAILABILITY

The present inventive concept relates to the method and the apparatus for automated detection of landmarks from 3D medical image data using deep learning and the patient's anatomical landmarks may be simply, quickly and accurately detected without a user input or an additional 3D model extracting process.

Although a few embodiments of the present inventive concept have been described, those skilled in the art will readily appreciate that many modifications are possible in the embodiments without materially departing from the novel teachings and advantages of the present inventive concept. Accordingly, all such modifications are intended to be included within the scope of the present inventive concept as defined in the claims.

The invention claimed is:

1. A method for automated detection of landmarks from 3D medical image data using deep learning, the method comprises:
   receiving a 3D volume medical image;
   generating a 2D intensity value projection image based on the 3D volume medical image;
   automatically detecting an initial anatomical landmark using a first convolutional neural network based on the 2D intensity value projection image;
   generating a 3D volume area of interest based on the initial anatomical landmark; and
   automatically detecting a detailed anatomical landmark using a second convolutional neural network different from the first convolutional neural network based on the 3D volume area of interest,
   wherein an input data of the first convolutional neural network is the 2D intensity value projection image and an output data of the first convolutional neural network is the initial anatomical landmark, and wherein an input data of the second convolutional neural network is the 3D volume area of interest and an output data of the second convolutional neural network is the detailed anatomical landmark.

2. The method of claim 1, wherein the 2D intensity value projection image is generated by projecting intensity values of the 3D volume medical image in one direction.

3. The method of claim 2, wherein a standard deviation of the intensity values of the 3D volume medical image is calculated in one direction to generate the 2D intensity value projection image.

4. The method of claim 1, wherein the 2D intensity value projection image includes a front intensity value projection image and a side intensity value projection image.

5. The method of claim 4, wherein the automatically detecting the initial anatomical landmark comprises passing the front intensity value projection image and the side intensity value projection image through the first convolutional neural network.

6. The method of claim 4, wherein the automatically detecting the initial anatomical landmark comprises:
detecting a front initial anatomical landmark based on the front intensity value projection image;
detecting a side initial anatomical landmark based on the side intensity value projection image; and
determining the initial anatomical landmark by combining the front initial anatomical landmark and the side initial anatomical landmark.

7. The method of claim 1, wherein the first convolutional neural network is a 2D fully convolutional deep neural network configured to output a 2D output based on a 2D input, and
wherein the second convolutional neural network is a 3D fully convolutional deep neural network configured to output a 3D output based on a 3D input.

8. The method of claim 7, wherein the output data of the first convolutional neural network includes a temporary initial anatomical landmark, wherein the output data of the first convolutional neural network is a 2D image having a greatest value at a position corresponding to the temporary initial anatomical landmark, and
wherein the output data of the second convolutional neural network includes a temporary detailed anatomical landmark, wherein the output data of the second convolutional neural network is a 3D volume image having a greatest value at a position corresponding to the temporary detailed anatomical landmark.

9. The method of claim 1, wherein the generating the 3D volume area of interest comprises extending from coordinates of the initial anatomical landmark in an x-axis direction, a y-axis direction, and a z-axis direction, respectively, and
wherein a central point of the 3D volume area of interest has the coordinates of the initial anatomical landmark.

10. The method of claim 1, wherein the detailed anatomical landmark includes first detailed landmarks disposed on a surface of a maxillofacial bone.

11. The method of claim 10, wherein the first detailed landmarks include Nasion, Anterior Nasal Spine, Point-A, Posterior Nasal Spine, Point-B, Pogonion, Gnathion, Right/Left of Orbitale Superius, Right/Left of Orbitale Inferius, Right/Left of Sutura Zygomaticofrontale, Right/Left of Foramen Mentale, Basion, Right Porion, Right/Left of *Condylus Medialis*, Right/Left of *Condylus Lateralis*, Right/Left of Areus Zygomatieus, Right/Left of Inferior Gonion, Right/Left of Posterior Gonion and Right of Processus Coronoideus.

12. The method of claim 10, wherein the detailed anatomical landmark includes a second detailed landmark disposed in a middle of a craniomaxillofacial soft tissue area.

13. The method of claim 12, wherein the second detailed landmark includes *Sella* which is a central point of *Sella turcica*.

14. The method of claim 12, wherein the detailed anatomical landmark includes third detailed landmarks disposed on a maxillofacial skin surface.

15. The method of claim 14, wherein the third detailed landmark includes *Glabella*, Soft Tissue Nasion, Pronasale, Subnasale, Upper Lip Superior, Lower Lip Superior, Soft Tissue Pogonion, Soft Tissue Gnathion and Soft Tissue B-point.

16. The method of claim 14, wherein the detailed anatomical landmark includes fourth detailed landmarks related with teeth and disposed inside of a jawbone.

17. The method of claim 16, wherein the fourth detailed landmarks include Central Incisor Root, First Molar Distal Root and Canine Root.

18. The method of claim 16, wherein the detailed anatomical landmark includes fifth detailed landmarks related with the teeth and disposed on the teeth.

19. The method of claim 18, wherein the fifth detailed landmarks include Mid Point of Central Incisors, Distal Point of First Molar Crown, Cusp Tip and Distal Point of Canine Crown.

20. A non-transitory computer-readable recording medium having recorded thereon at least one program comprising commands, which when executed by a computer, performs the method of one of claim 1.

21. An apparatus for automated detection of landmarks from 3D medical image data using deep learning, the apparatus comprises:
an intensity value projection image generator configured to receive a 3D volume medical image and to generate a 2D intensity value projection image based on the 3D volume medical image;
an initial landmark automatic detector configured to automatically detect an initial anatomical landmark using a first convolutional neural network based on the 2D intensity value projection image;
a 3D volume area of interest generator configured to receive the 3D volume medical image and to generate a 3D volume area of interest from the 3D volume medical image based on the initial anatomical landmark; and
a detailed landmark automatic detector configured to automatically detect a detailed anatomical landmark using a second convolutional neural network different from the first convolutional neural network based on the 3D volume area of interest,
wherein an input data of the first convolutional neural network is the 2D intensity value projection image and an output data of the first convolutional neural network is the initial anatomical landmark, and
wherein an input data of the second convolutional neural network is the 3D volume area of interest and an output data of the second convolutional neural network is the detailed anatomical landmark.

* * * * *